(12) United States Patent
Liu et al.

(10) Patent No.: US 10,471,397 B2
(45) Date of Patent: Nov. 12, 2019

(54) HIGH PERFORMANCE FACILITATED TRANSPORT MEMBRANES FOR OLEFIN/PARAFFIN SEPARATIONS

(71) Applicant: UOP LLC, Des Plaines, IL (US)

(72) Inventors: Chunqing Liu, Arlington Heights, IL (US); Nicole K. Karns, Chicago, IL (US)

( * ) Notice: Subject to any disclaimer, the term of this patent is extended or adjusted under 35 U.S.C. 154(b) by 0 days.

(21) Appl. No.: 16/402,997

(22) Filed: May 3, 2019

(65) Prior Publication Data

US 2019/0255490 A1   Aug. 22, 2019

Related U.S. Application Data

(62) Division of application No. 15/610,305, filed on May 31, 2017, now Pat. No. 10,322,382.

(51) Int. Cl.
| | |
|---|---|
| *B01D 71/64* | (2006.01) |
| *B01D 71/82* | (2006.01) |
| *B01D 67/00* | (2006.01) |
| *B01D 53/22* | (2006.01) |
| *B01D 69/08* | (2006.01) |
| *B01D 69/12* | (2006.01) |
| *B01D 69/06* | (2006.01) |
| *B01D 71/02* | (2006.01) |
| *C07C 7/144* | (2006.01) |

(52) U.S. Cl.
CPC ............ *B01D 71/64* (2013.01); *B01D 53/228* (2013.01); *B01D 67/0079* (2013.01); *B01D 67/0093* (2013.01); *B01D 69/06* (2013.01); *B01D 69/08* (2013.01); *B01D 69/12* (2013.01); *B01D 71/022* (2013.01); *B01D 71/82* (2013.01); *C07C 7/144* (2013.01)

(58) Field of Classification Search
None
See application file for complete search history.

(56) References Cited

U.S. PATENT DOCUMENTS

| | | | |
|---|---|---|---|
| 2018/0001277 A1* | 1/2018 | Liu | B01D 67/0079 |
| 2019/0100479 A1* | 4/2019 | Liu | C07C 7/005 |
| 2019/0193021 A1* | 6/2019 | Rekoske | B01D 53/226 |

* cited by examiner

*Primary Examiner* — Tam M Nguyen

(57) ABSTRACT

A high performance facilitated transport membrane comprising a metal cation exchanged/chelated carboxylic acid functional group containing functional polyimide, a method of making this a membrane, and the use of this membrane for olefin/paraffin separations, particularly for propylene/propane and ethylene/ethane separations. The facilitated transport membrane has either an asymmetric integrally skinned membrane structure or a thin film composite membrane structure, wherein the top selective layer of the membrane comprises a metal cation exchanged/chelated carboxylic acid functional group containing functional polyimide.

9 Claims, No Drawings

HIGH PERFORMANCE FACILITATED TRANSPORT MEMBRANES FOR OLEFIN/PARAFFIN SEPARATIONS

CROSS-REFERENCE TO RELATED APPLICATION

This application is a divisional application of application Ser. No. 15/610,305, filed on May 31, 2017, now U.S. patent Ser. No. 10/322,382, which claims priority from Provisional Application No. 62/357,213 filed Jun. 30, 2016, the contents of which cited application are hereby incorporated by reference in its entirety.

BACKGROUND OF THE INVENTION

Light olefins, such as propylene and ethylene, are produced as co-products from a variety of feed stocks in a number of different processes in the chemical, petrochemical, and petroleum refining industries. Various petrochemical streams contain olefins and other saturated hydrocarbons. Typically, these streams are from steam cracking units (ethylene production), catalytic cracking units (motor gasoline production), or the dehydrogenation of paraffins.

Currently, the separation of olefin and paraffin components is performed by cryogenic distillation, which is expensive and energy intensive due to the low relative volatilities of the components. Large capital expense and energy costs have created incentives for extensive research in this area of separations, and low energy-intensive membrane separations have been considered as an attractive alternative.

In principle, membrane-based technologies have advantages of both low capital cost and high-energy efficiency compared to conventional separation methods for olefin/paraffin separations, such as propylene/propane and ethylene/ethane separations. Four main types of membranes have been reported for olefin/paraffin separations including facilitated transport membranes, polymer membranes, mixed matrix membranes, and inorganic membranes. Facilitated transport membranes, or ion exchange membranes, which sometimes use silver ions as a complexing agent, have very high olefin/paraffin separation selectivity. However, poor chemical stability due to carrier poisoning or loss, high cost, and low flux currently limit practical applications of facilitated transport membranes.

Separation of olefins from paraffins via conventional polymer membranes has not been commercially successful due to inadequate selectivities and permeabilities of the polymeric membrane materials, as well as plasticization issues. Polymers that are more permeable are generally less selective than are less permeable polymers. A general trade-off exists between permeability and selectivity of the polymeric membrane materials (the so-called "polymer upper bound limit") for all kinds of separations, including olefin/paraffin separations. In recent years, substantial research effort has been directed to overcoming the limits imposed by this upper bound. Various polymers and techniques have been used, but without much success in terms of improving the membrane selectivity.

Much more efforts have been undertaken to develop metal ion incorporated, high olefin/paraffin selectivity facilitated transport membranes. The high selectivity for olefin/paraffin is achieved by the incorporation of metal ions such as silver (I) or copper (I) cations into a solid nonporous polymer matrix layer on top of a highly porous membrane support layer (so-called "fixed site carrier facilitated transport membrane") or directly into the pores of the highly porous support membrane (so-called "supported liquid facilitated transport membrane") that results in the formation of a reversible metal cation complex with the pi bond of olefins, whereas no interaction occurs between the metal cations and the paraffins. Addition of water, plasticizer, or humidification of the olefin/paraffin feed streams to either the fixed site carrier facilitated transport membranes or the supported liquid facilitated transport membranes is usually required to obtain reasonable olefin permeances and high olefin/paraffin selectivities. The performance of fixed site carrier facilitated transport membranes is much more stable than that of the supported liquid facilitated transport membranes. The fixed site carrier facilitated transport membranes are less sensitive to the loss of metal cation carriers than the supported liquid facilitated transport membranes.

Pinnau et al. disclosed a solid polymer electrolyte fixed site carrier facilitated transport membrane comprising silver tetrafluoroborate incorporated poly(ethylene oxide), see U.S. Pat. No. 5,670,051. Herrera et al. disclosed a process for the separation of olefin/paraffin using a silver cation-chelated chitosan fixed site carrier facilitated transport membrane, see U.S. Pat. No. 7,361,800. Herrera et al. disclosed the coating of a layer of chitosan on the surface of a microporous support membrane, wherein the support membrane is made from polyesters, polyamides, polyimides, polyvinylidene fluoride, polyacrylonitrile, polysulfones or polycarbonates. Common composite facilitated transport membranes comprise ultrafiltration or microfiltration membrane as the support membrane.

Feiring et al. disclosed a new facilitated transport membrane comprising silver (I) cation exchanged fluorinated copolymer synthesized from a perfluorinated cyclic or cyclizable monomer and a strong acid highly fluorinated vinylether compound. The membrane, however, did not show olefin to paraffin selectivity higher than 200, see US 2015/0025293.

The composite facilitated transport membranes disclosed in the literature comprise an ultrafiltration or microfiltration membrane as the support membrane. The use of a relatively hydrophilic, nanoporous polymeric membrane such as polyethersulfone membrane as the support membrane for the preparation of fixed site carrier facilitated transport membranes for olefin/paraffin separations has not been reported in the literature. In particular, the use of a relatively hydrophilic, very small pore, nanoporous support membrane with an average pore diameter of less than 10 nm on the membrane skin layer surface for the preparation of fixed site carrier facilitated transport membranes has not been disclosed in the literature.

Development of new stable, high permeance, and high selectivity facilitated transport membranes is critical for the future success in the use of membranes for olefin/paraffin separations such as propylene/propane separation.

SUMMARY OF THE INVENTION

This invention discloses a new high performance facilitated transport membrane comprising a carboxylic acid functional group containing polyimide wherein the carboxylic acid functional groups are ion-exchanged or chelated with metal cations such as silver (I) or copper (I) cations, a method of making such a membrane, and the use of such a membrane for olefin/paraffin separations, particularly for propylene/propane (C3=/C3) and ethylene/ethane (C2=/C2) separations.

The new high performance facilitated transport membrane disclosed in the present invention comprises a carboxylic acid functional group containing polyimide wherein the carboxylic acid functional groups are ion-exchanged or chelated with metal cations such as silver (I) or copper (I) cations. The new high performance facilitated transport membrane disclosed in the present invention has either an asymmetric integrally skinned membrane structure or a thin film composite membrane structure, wherein at least the top selective layer of the membrane comprises a carboxylic acid functional group containing polyimide, and wherein the carboxylic acid functional groups are ion-exchanged or chelated with metal cations such as silver (I) or cupper (I) cations. Different from the facilitated transport membranes reported by Pinnau et al. (U.S. Pat. No. 5,670,051), Herrera et al. (U.S. Pat. No. 7,361,800), Feiring et al. (US 2015/0025293), the current invention discloses a new high performance facilitated transport membrane comprising a carboxylic acid functional group containing polyimide wherein the carboxylic acid functional groups are ion-exchanged or chelated with metal cations such as silver (I) or copper (I) cations to form said facilitated transport membrane with stable separation performance. The present invention teaches the use of carboxylic acid functional group containing polyimide for the preparation of the new facilitated transport membrane for olefin/paraffin separation. The use of a polyimide comprising carboxylic acid functional groups in the present invention is to stabilize the metal cations in the new high performance facilitated transport membrane and also to provide asymmetric integrally skinned or thin film composite membrane structure. The polyimide comprising carboxylic acid functional groups can be easily fabricated into asymmetric membranes. The carboxylic acid functional groups on the polyimide can be ion-exchanged or chelated with the metal cations such as silver (I) cations to form the facilitated transport membrane with stable separation performance.

The facilitated transport membranes comprising a carboxylic acid functional group containing polyimide wherein the carboxylic acid functional groups are ion-exchanged or chelated with metal cations such as silver (I) or copper (I) cations described in the current invention showed high olefin/paraffin selectivity, high olefin permeance, and stable performance over time. The high selectivity and high permeance of the facilitated transport membranes described in the current invention is achieved by the formation of a reversible metal cation complex with the pi bond of olefins, whereas no interaction occurs between the metal cations and the paraffins.

One new high performance facilitated transport membrane 1.5 MAg+/PI-50 described in the present invention with an asymmetric integrally skinned flat sheet membrane structure was fabricated from carboxylic acid containing poly(2,2'-bis-(3,4-dicarboxyphenyl) hexafluoropropane dianhydride-3,5-diaminobenzoic acid-3,3'-dihydroxy-4,4'-diamino-biphenyl) polyimide (abbreviated as PI-50) that was synthesized from 2,2'-bis-(3,4-dicarboxyphenyl) hexafluoropropane dianhydride (6FDA) and a mixture of 3,5-diaminobenzoic acid (3,5-DBA) and 3,3'-dihydroxy-4,4'-diamino-biphenyl (HAB) (molar ratio of 3,5-DBA/HAB=1:4), wherein the carboxylic acid functional groups on PI-50 were ion-exchanged or chelated with silver (I) cation. Permeation testing experiments using humidified (relative humidity 80-100%) propylene and propane mixed vapor phase feed (30% propylene and 70% propane at 791 kPa (100 psig) and 35° C.) showed that this 1.5 MAg+/PI-50 membrane had both high propylene (C3=) permeance ($P_{C3=}/L$=259 GPU) and high propylene/propane (C3=/C3) selectivity ($\alpha_{C3=/C3}$=466). Permeation testing experiments using humidified (relative humidity 80-100%) propylene and propane mixed vapor phase feed (70% propylene and 30% propane at 791 kPa (100 psig) and 35° C.) also showed that this 1.5 MAg+/PI-50 membrane had both high propylene (C3=) permeance ($P_{C3=}/L$=192 GPU) and high propylene/propane (C3=/C3) selectivity ($\alpha_{C3=/C3}$=~1000).

Another new high performance facilitated transport membrane 3 MAg+/PI-150 described in the present invention with an asymmetric integrally skinned membrane flat sheet structure was fabricated from carboxylic acid containing poly(2,2'-bis-(3,4-dicarboxyphenyl) hexafluoropropane dianhydride-3,5-diaminobenzoic acid-3,3',5,5'-tetramethyl-4,4'-methylene dianiline) polyimide (abbreviated as PI-150) derived from the polycondensation reaction of 6FDA and a mixture of 3,5-DBA and 3,3',5,5'-tetramethyl-4,4'-methylene dianiline (TMMDA) (molar ratio of 3,5-DBA/TMMDA=2:1), wherein the carboxylic acid functional groups on PI-150 were ion-exchanged or chelated with silver cation. Permeation testing experiments using humidified (relative humidity 80-100%) propylene and propane mixed vapor phase feed (30% propylene and 70% propane at 791 kPa (100 psig) and 35° C.) showed that this 3 MAg+/PI-150 membrane has both high propylene (C3=) permeance ($P_{C3=}/L$=147 GPU) and high propylene/propane (C3=/C3) selectivity ($\alpha_{C3=/C3}$=239).

The new high performance facilitated transport membrane comprising a carboxylic acid functional group containing polyimide wherein the carboxylic acid functional groups are ion-exchanged or chelated with metal cations such as silver (I) or copper (I) cations disclosed in the present invention also showed much more stable membrane performance than the metal cation impregnated asymmetric polymeric facilitated transport membranes without any carboxylic acid functional groups such as silver (I) cation impregnated asymmetric polyethersulfone membrane with silver (I) cation impregnated in the top selective layer of the membrane.

The present invention also discloses a method of making the new high performance facilitated transport membrane comprising a carboxylic acid functional group containing polyimide wherein the carboxylic acid functional groups are ion-exchanged or chelated with metal cations such as silver or copper (I) cations. The method comprises: 1) preparation of an asymmetric carboxylic acid functional group containing a polyimide flat sheet or a hollow fiber membrane with either an asymmetric integrally skinned or a thin film composite membrane structure, wherein at least the top selective layer of the membrane comprises a carboxylic acid functional group containing polyimide; 2) preparation of the facilitated transport membrane by ion-exchanging or chelating the carboxylic acid functional groups on the polyimide polymer of the asymmetric carboxylic acid functional group containing the polyimide flat sheet or the hollow fiber membrane prepared in step 1) with metal cations such as silver (I) or copper (I) cations. The top selective layer surface of the asymmetric carboxylic acid functional group containing the polyimide flat sheet or hollow fiber membrane prepared in step 1) was soaked in a metal cation aqueous solution such as silver nitrate ($AgNO_3$) aqueous solution for a sufficient time to form the facilitated transport membrane comprising metal cation ion-exchanged or chelated carboxylic acid functional group containing polyimide.

The present invention provides a process for separating olefin from a mixture of olefin and paraffin using the new high performance facilitated transport membrane comprising a carboxylic acid functional group containing polyimide wherein the carboxylic acid functional groups are ion-exchanged or chelated with metal cations such as silver (I) or copper (I) cations described in the present invention, the process comprising: (a) providing a new high performance facilitated transport membrane comprising a carboxylic acid functional group containing polyimide wherein the carboxylic acid functional groups are ion-exchanged or chelated with metal cations such as silver (I) or copper (I) cations described in the present invention which is permeable to said olefin; (b) contacting the humidified olefin/paraffin mixture feed on one side of the new high performance facilitated transport membrane comprising a carboxylic acid functional group containing polyimide wherein the carboxylic acid functional groups are ion-exchanged or chelated with metal cations such as silver (I) or copper (I) cations described in the present invention to cause said olefin to permeate the membrane; and (c) removing from the opposite side of the membrane a permeate gas composition comprising a portion of said olefin which permeated through said membrane.

DETAILED DESCRIPTION OF THE INVENTION

Membrane technology has been of great interest for the separation of olefin/paraffin mixtures. However, despite significant research effort on olefin/paraffin separations by membrane technology, no commercial olefin/paraffin separation application using membranes has been reported.

The present invention discloses a new high performance facilitated transport membrane comprising a carboxylic acid functional group containing polyimide wherein the carboxylic acid functional groups are ion-exchanged or chelated with metal cations such as silver (I) or copper (I) cations. The present invention further discloses a method of making such a membrane and the use of such a membrane for olefin/paraffin separations, particularly for propylene/propane (C3=/C3) and ethylene/ethane (C2=/C2) separations.

The new high performance facilitated transport membrane disclosed in the present invention comprises a carboxylic acid functional group containing polyimide wherein the carboxylic acid functional groups are ion-exchanged or chelated with metal cations such as silver (I) or copper (I) cations. The metal cation ion-exchanged or chelated carboxylic acid functional group containing polyimide described in the current invention comprising a plurality of repeating units of formula (I)

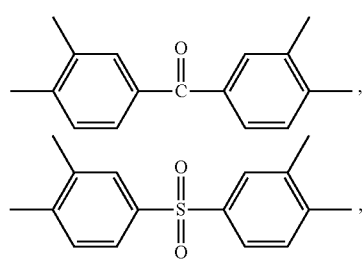

wherein $X_1$ and $X_2$ are selected from the group consisting of

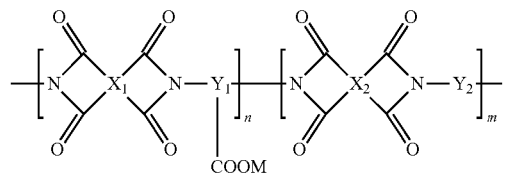

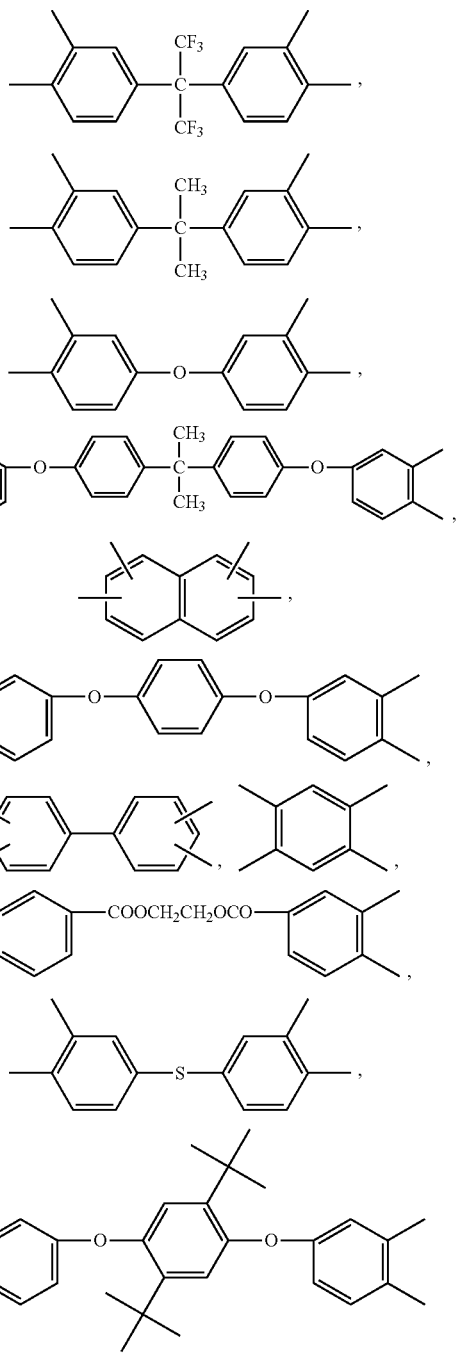

and mixtures thereof, and wherein X1 and X2 may be the same or different from each other; wherein $Y_1$—COOM is selected from the group consisting of

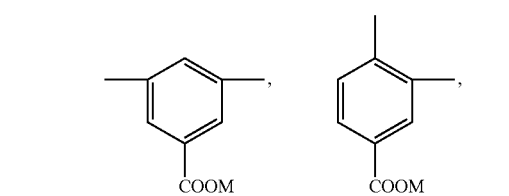

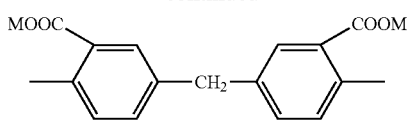

and mixtures thereof and wherein M is selected from silver (I) cation or copper (I) cation; wherein Y2 is selected from the group consisting of

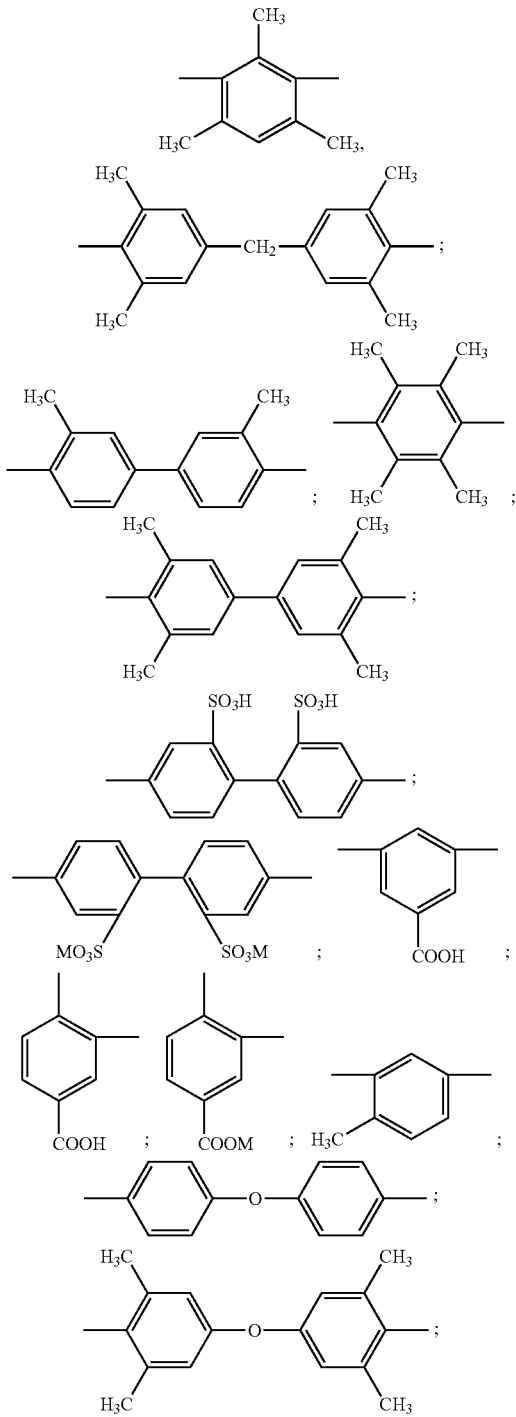

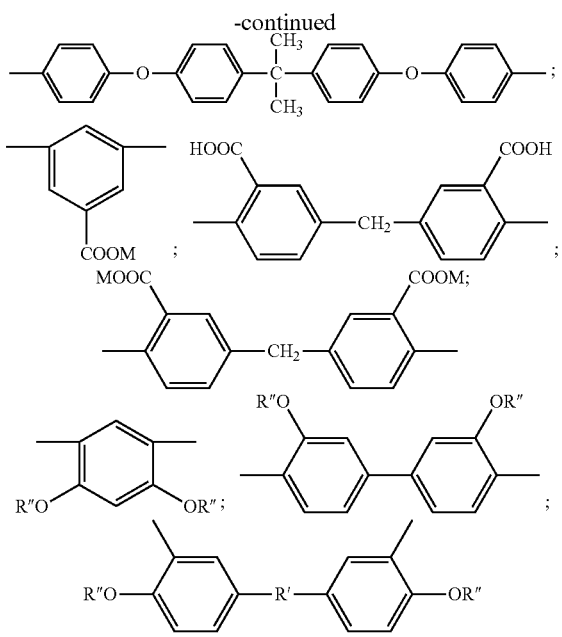

and mixtures thereof, and —R'— is selected from the group consisting of

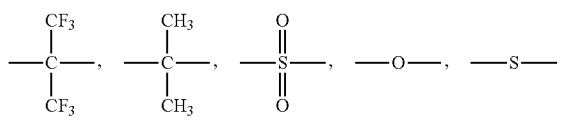

and mixtures thereof, and —R"— is selected from the group consisting of —H, COCH$_3$, and mixtures thereof, and M is selected from silver (I) cation or copper (I) cation; wherein n and m are independent integers from 2 to 500; and wherein n/m is in a range of 1:0 to 1:10, and preferably n/m is in a range of 1:0 to 1:5.

Preferably, X$_1$ and X$_2$ are selected from the group consisting of

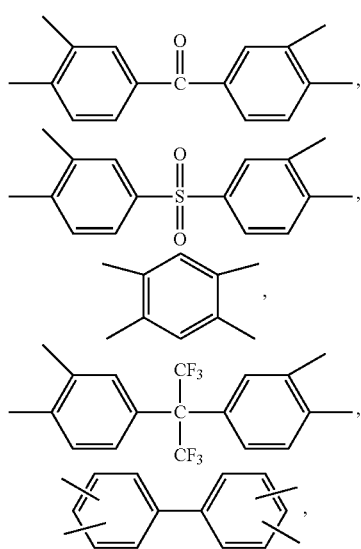

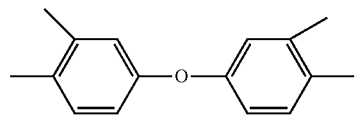

and mixtures thereof, and wherein X1 and X2 may be the same or different from each other; preferably Y₁—COOM is selected from the group consisting of

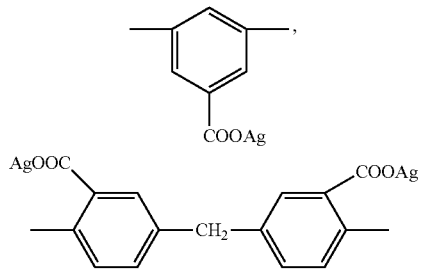

and mixtures thereof; preferably Y2 is selected from the group consisting of

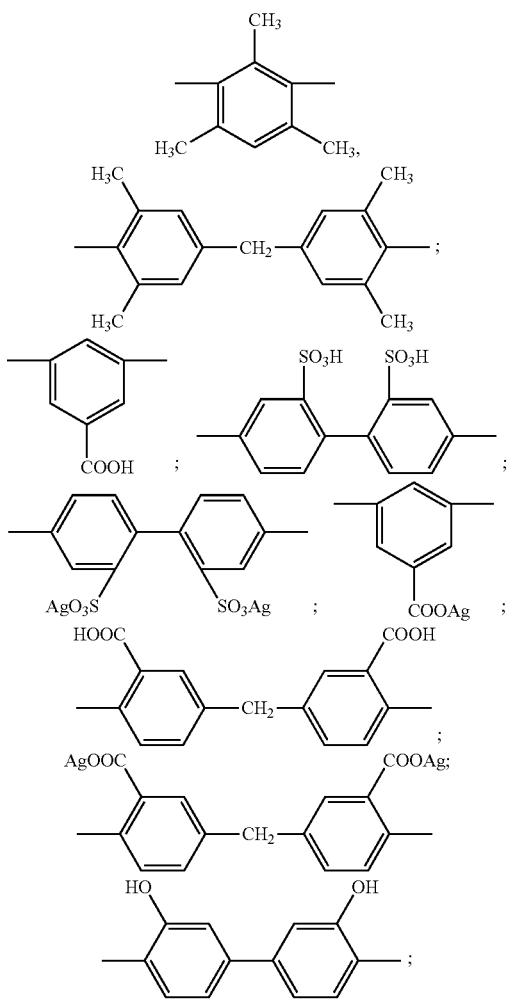

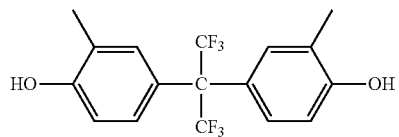

and mixtures thereof.

The carboxylic acid functional group containing polyimide used for the preparation the new high performance facilitated transport membrane comprising a carboxylic acid functional group containing polyimide wherein the carboxylic acid functional groups are ion-exchanged or chelated with metal cations such as silver (I) or copper (I) cations described in the current invention comprising a plurality of repeating units of formula (II)

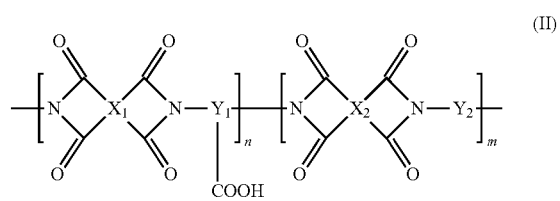

wherein $X_1$ and $X_2$ are selected from the group consisting of

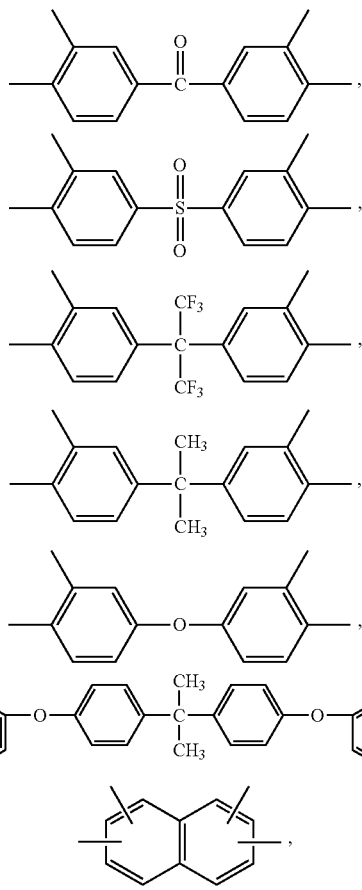

-continued
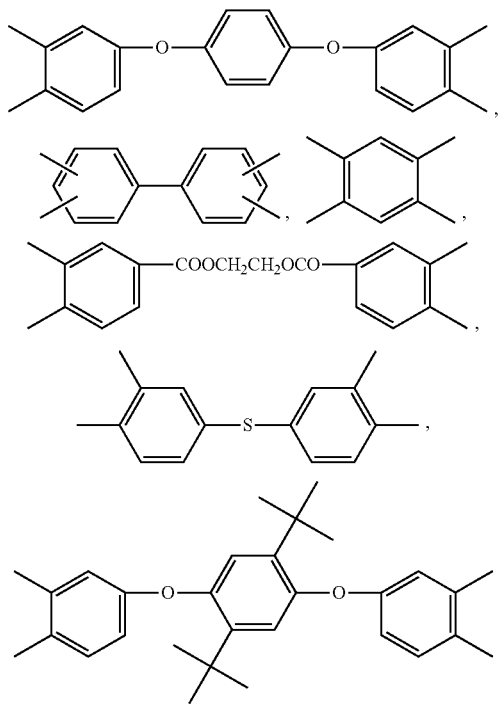
and mixtures thereof, and wherein X1 and X2 may be the same or different from each other; wherein Y$_1$—COOH is selected from the group consisting of
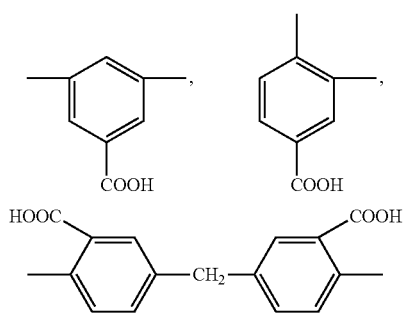
and mixtures thereof; wherein Y2 is selected from the group consisting of
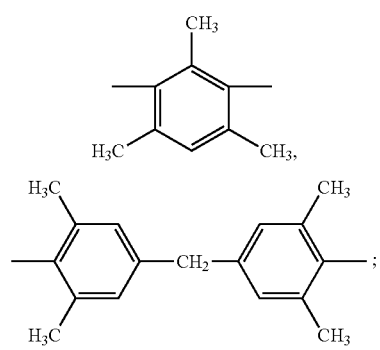
-continued
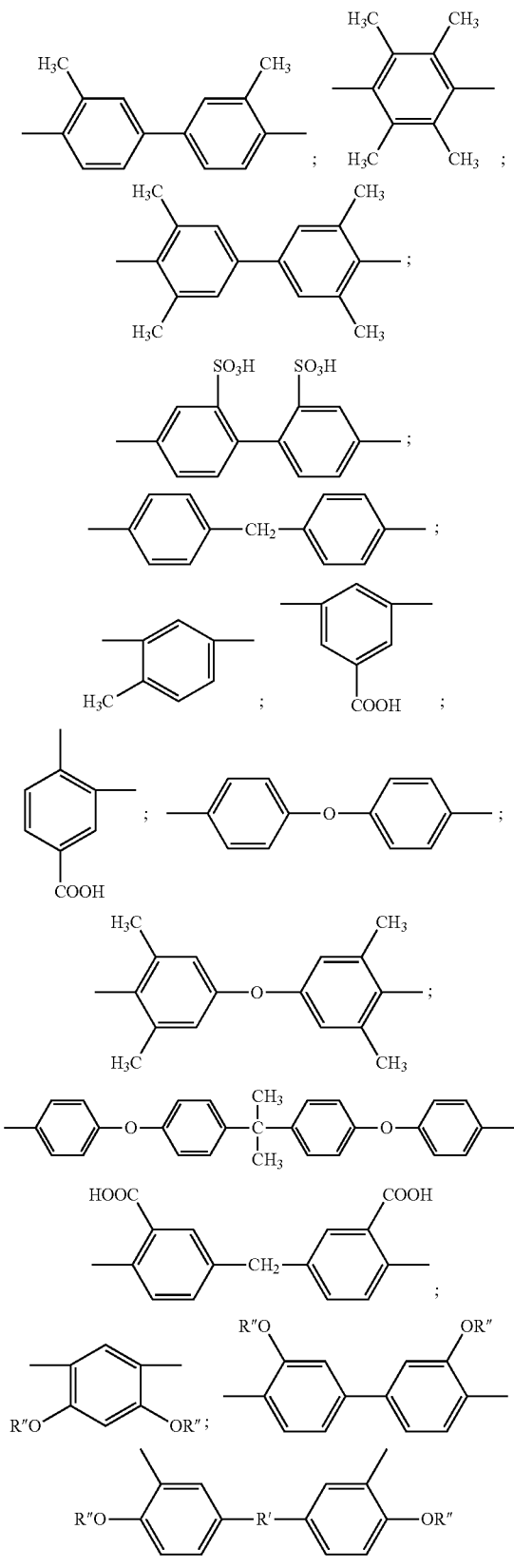
and mixtures thereof, and —R'— is selected from the group consisting of

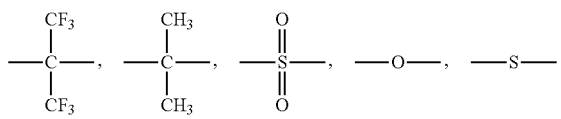

and mixtures thereof, and —R"— is selected from the group consisting of —H, COCH$_3$, and mixtures thereof; wherein n and m are independent integers from 2 to 500; and wherein n/m is in a range of 1:0 to 1:10, and preferably n/m is in a range of 1:0 to 1:5.

Preferably, X$_1$ and X$_2$ are selected from the group consisting of

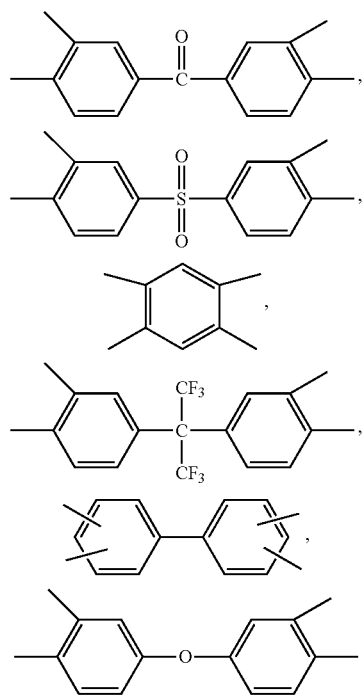

and mixtures thereof, and wherein X1 and X2 may be the same or different from each other; preferably Y$_1$—COOH is selected from the group consisting of

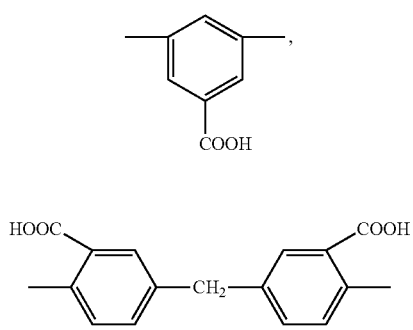

and mixtures thereof; preferably Y2 is selected from the group consisting of

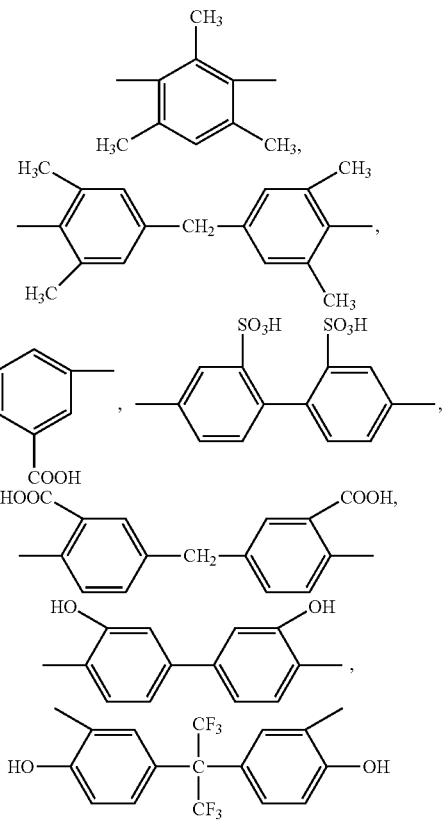

and mixtures thereof, and —R"— is selected from the group consisting of —H, COCH$_3$, and mixtures thereof.

The carboxylic acid functional group containing polyimide comprising a plurality of repeating units of formula (II) used for the preparation the new high performance facilitated transport membrane comprising a carboxylic acid functional group containing polyimide wherein the carboxylic acid functional groups are ion-exchanged or chelated with metal cations such as silver (I) or copper (I) cations of the invention may be selected from, but is not limited to, the group consisting of poly(2,2'-bis-(3,4-dicarboxyphenyl) hexafluoropropane dianhydride-3,5-diaminobenzoic acid-3, 3'-dihydroxy-4,4'-diamino-biphenyl) polyimides derived from a polycondensation reaction of 2,2'-bis-(3,4-dicarboxyphenyl)hexafluoropropane dianhydride (6FDA) with a mixture of 3,5-diaminobenzoic acid (3,5-DBA) and 3,3'-dihydroxy-4,4'-diamino-biphenyl (HAB) and the molar ratio of 3,5-DBA to HAB may be in a range of 1:0 to 1:5, poly(2, 2'-bis-(3,4-dicarboxyphenyl)hexafluoropropane dianhydride-3,5-diaminobenzoic acid-3,3',5,5'-tetramethyl-4,4'-methylene dianiline) polyimides derived from the polycondensation reaction of 6FDA and a mixture of 3,5-DBA and 3,3',5,5'-tetramethyl-4,4'-methylene dianiline (TMMDA) and the molar ratio of 3,5-DBA to TMMDA may be in a range of 1:0 to 1:5, poly(6FDA-3,5-DBA), poly(2, 2'-bis-(3,4-dicarboxyphenyl)hexafluoropropane dianhydride-3,3'-methylenebis(6-aminobenzoic acid)-3,3',5,5'-tetramethyl-4,4'-methylene dianiline) polyimides derived from the polycondensation reaction of 6FDA and a mixture of 3,3'-methylenebis(6-aminobenzoic acid) (MBA) and TMMDA and the molar ratio of MBA to TMMDA may be in a range of 1:0 to 1:5, poly(6FDA-MBA), poly(6FDA-MBA-HAB)s and the molar ratio of MBA to HAB may be in a range of 1:0 to 1:5, poly(3,3',4,4'-diphenylsulfone tetracarboxylic dianhydride-3,5-diaminobenzoic acid-3,3'-dihydroxy-4,4'-diamino-biphenyl) polyimides derived from a polycondensation reaction of 3,3',4,4'-diphenylsulfone tetracarboxylic dianhydride (DSDA) with a mixture of 3,5-DBA and HAB and the molar ratio of 3,5-DBA to HAB may be in a range of 1:0 to 1:5, poly(DSDA-3,5-DBA-TMMDA)s and the molar ratio of 3,5-DBA to TMMDA may be in a range of 1:0 to 1:5, poly(DSDA-MBA-TMMDA)s and the molar ratio of MBA to TMMDA may be in a range of 1:0 to 1:5, poly(DSDA-MBA-HAB)s and the molar ratio of MBA to HAB may be in a range of 1:0 to 1:5, poly(DSDA-3,5-DBA), poly(DSDA-MBA), poly(DSDA-3,5-DBA-MBA)s and the molar ratio of 3,5-DBA to MBA may be in a range of 1:0 to 1:5, poly(3,3',4,4'-diphenylsulfone tetracarboxylic dianhydride-3,4-diaminobenzoic acid-3,3'-dihydroxy-4,4'-diamino-biphenyl) polyimides derived from a polycondensation reaction of DSDA with a mixture of 3,4-DBA and HAB and the molar ratio of 3,4-DBA to HAB may be in a range of 1:0 to 1:5, poly(6FDA-3,4-DBA-HAB)s and the molar ratio of 3,4-DBA to HAB may be in a range of 1:0 to 1:5, poly(3,3',4,4'-benzophenone tetracarboxylic dianhydride-pyromellitic dianhydride-3,5-diaminobenzoic acid-3,3'-dihydroxy-4,4'-diamino-biphenyl) polyimides derived from a polycondensation reaction of a mixture of 3,3',4,4'-benzophenone tetracarboxylic dianhydride (BTDA) and pyromellitic dianhydride (PMDA) with a mixture of 3,5-DBA and HAB and the molar ratio of 3,5-DBA to HAB may be in a range of 1:0 to 1:5 and the molar ratio of BTDA to PMDA may be in a range of 2:1 to 1:2, poly(BTDA-PMDA-MBA-HAB)s and the molar ratio of MBA to HAB may be in a range of 1:0 to 1:5 and the molar ratio of BTDA to PMDA may be in a range of 2:1 to 1:2, poly(BTDA-PMDA-MBA-TMMDA)s and the molar ratio of MBA to TMMDA may be in a range of 1:0 to 1:5 and the molar ratio of BTDA to PMDA may be in a range of 2:1 to 1:2, poly(BTDA-PMDA-3,5-DBA-TMMDA)s and the molar ratio of 3,5-DBA to TMMDA may be in a range of 1:0 to 1:5 and the molar ratio of BTDA to PMDA may be in a range of 2:1 to 1:2, and blends thereof.

The new high performance facilitated transport membrane disclosed in the present invention has either an asymmetric integrally skinned membrane structure or a thin film composite membrane structure, wherein at least the top selective layer of the membrane comprises a carboxylic acid functional group containing polyimide, and wherein the carboxylic acid functional groups are ion-exchanged or chelated with metal cations such as silver or copper (I) cations. Both the top selective layer and the highly porous support layer underneath the top selective layer of the asymmetric integrally skinned facilitated transport membranes disclosed in the present invention comprise a carboxylic acid functional group containing polyimide, and wherein the carboxylic acid functional groups are ion-exchanged or chelated with metal cations such as silver (I) or copper (I) cations. The asymmetric integrally skinned membranes comprising a carboxylic acid functional group containing polyimide for the preparation of the high performance facilitated transport membranes disclosed in the present invention are fabricated via a phase inversion technique.

The facilitated transport membrane comprising a carboxylic acid functional group containing polyimide wherein the carboxylic acid functional groups are ion-exchanged or chelated with metal cations such as silver (I) or copper (I) cations described in the present invention can be fabricated into any convenient form suitable for a desired application. For example, the membranes can be in the form of hollow fibers, tubes, flat sheets, and the like. The membranes can also be in the form of thin film composite comprising a carboxylic acid functional group containing polyimide selective layer wherein the carboxylic acid functional groups are ion-exchanged or chelated with metal cations such as silver (I) or copper (I) cations and a porous supporting layer comprising a polymer material different from the carboxylic acid functional group containing polyimide described in the current invention or an inorganic material. The form of the membrane may depend upon the nature of the membrane itself and the ease of manufacturing the form. The membrane can be assembled in a separator in any suitable configuration for the form of the membrane and the separator may provide for co-current, counter-current, or cross-current flows of the feed on the retentate and permeate sides of the membrane. In one exemplary embodiment a facilitated transport membrane comprising a carboxylic acid functional group containing polyimide wherein the carboxylic acid functional groups are ion-exchanged or chelated with metal cations such as silver (I) or copper (I) cations for olefin/paraffin separations in a spiral wound module is in the form of flat sheet having a thickness from about 30 to about 400 µm. In another exemplary embodiment a facilitated transport membrane comprising a carboxylic acid functional group containing polyimide wherein the carboxylic acid functional groups are ion-exchanged or chelated with metal cations such as silver (I) or copper (I) cations for olefin/paraffin separations is in a hollow fiber module that is in the form of thousands, tens of thousands, hundreds of thousands, or more, of parallel, closely-packed hollow fibers or tubes. In one embodiment, each fiber has an outside diameter of from about 200 micrometers (µm) to about 700 millimeters (mm) and a wall thickness of from about 30 to about 200 µm. In operation, a feed contacts a first surface of the membrane, a permeate permeates the membrane and is removed therefrom, and a retentate, not having permeated the membrane, also is removed therefrom. In another embodiment, a facilitated transport membrane comprising a carboxylic acid functional group containing polyimide wherein the carboxylic acid functional groups are ion-exchanged or chelated with metal cations such as silver (I) or copper (I) cations for olefin/paraffin separations can be in the form of flat sheet having a thickness in the range of from about 30 to about 400 µm.

Different from the facilitated transport membranes reported by Pinnau et al. (U.S. Pat. No. 5,670,051), Herrera et al. (U.S. Pat. No. 7,361,800), Feiring et al. (US 2015/0025293), the current invention discloses a new high performance facilitated transport membrane comprising a carboxylic acid functional group containing polyimide wherein the carboxylic acid functional groups are ion-exchanged or chelated with metal cations such as silver (I) or copper (I) cations to form said facilitated transport membrane with stable separation performance. The present invention teaches the use of carboxylic acid functional group containing polyimide for the preparation of the new facilitated transport membrane for olefin/paraffin separation. The use of polyimide comprising carboxylic acid functional groups in the present invention is to stabilize the metal cations in the new high performance facilitated transport membrane and also to provide asymmetric integrally skinned or thin film composite membrane structure. The polyimide comprising carboxylic acid functional groups in the present invention can be easily fabricated into asymmetric membranes. The carboxylic acid functional groups on the polyimide can be ion-exchanged or chelated with the metal cations such as silver cation to form said facilitated transport membrane with stable separation performance.

The facilitated transport membranes comprising a carboxylic acid functional group containing polyimide wherein the carboxylic acid functional groups are ion-exchanged or chelated with metal cations such as silver (I) or copper (I) cations described in the current invention showed high olefin/paraffin selectivity, high olefin permeance, and stable performance over time. The high selectivity and high permeance of the facilitated transport membranes described in the current invention is achieved by the formation of a reversible metal cation complex with the pi bond of olefins, whereas no interaction occurs between the metal cations and the paraffins.

The new high performance facilitated transport membrane comprising a carboxylic acid functional group containing polyimide wherein the carboxylic acid functional groups are ion-exchanged or chelated with metal cations such as silver (I) or copper (I) cations disclosed in the present invention also showed much more stable membrane performance than the metal cation impregnated asymmetric polymeric facilitated transport membranes without any carboxylic acid functional groups such as silver cation impregnated asymmetric polyethersulfone membrane with silver cation impregnated in the top selective layer of the membrane.

The present invention also discloses a method of making the new high performance facilitated transport membrane comprising a carboxylic acid functional group containing polyimide wherein the carboxylic acid functional groups are ion-exchanged or chelated with metal cations such as silver (I) or copper (I) cations. The method comprises: 1) Preparation of asymmetric carboxylic acid functional group containing polyimide flat sheet or hollow fiber membrane with either asymmetric integrally skinned or thin film composite membrane structure, wherein at least the top selective layer of said membrane comprises a carboxylic acid functional group containing polyimide; 2) Preparation of the facilitated transport membrane by ion-exchanging or chelating the carboxylic acid functional groups on the polyimide polymer of said asymmetric carboxylic acid functional group containing polyimide flat sheet or hollow fiber membrane prepared in step 1) with metal cations such as silver (I) or copper (I) cations. The top selective layer surface of said asymmetric carboxylic acid functional group containing polyimide flat sheet or hollow fiber membrane prepared in step 1) was soaked in a metal cation aqueous solution such as silver nitrate ($AgNO_3$) aqueous solution for a certain time to form the facilitated transport membrane comprising metal cation ion-exchanged or chelated carboxylic acid functional group containing polyimide.

The present invention provides a process for the separation of paraffin and olefin, such as, for example, in gaseous streams produced from steam cracking, catalytic cracking, the dehydration of paraffins, and the like using the new high performance facilitated transport membrane comprising a carboxylic acid functional group containing polyimide wherein the carboxylic acid functional groups are ion-exchanged or chelated with metal cations such as silver (I) or copper (I) cations described in the present invention, and the process comprises: (a) providing a new high performance facilitated transport membrane comprising a carboxylic acid functional group containing polyimide wherein the carboxylic acid functional groups are ion-exchanged or chelated with metal cations such as silver (I) or copper (I) cations described in the present invention which is permeable to said olefin; (b) contacting the humidified olefin/paraffin mixture feed on one side of the new high performance facilitated transport membrane comprising a carboxylic acid functional group containing polyimide wherein the carboxylic acid functional groups are ion-exchanged or chelated with metal cations such as silver (I) or copper (I) cations described in the present invention to cause said olefin to permeate the membrane; and (c) removing from the opposite side of the membrane a permeate gas composition comprising a portion of said olefin which permeated through said membrane. The process utilizes a facilitated transport membrane comprising a carboxylic acid functional group containing polyimide wherein the carboxylic acid functional groups are ion-exchanged or chelated with metal cations such as silver (I) or copper (I) cations described in the present invention that is highly permeable but also highly selective to olefin, thus permitting olefin to permeate the membrane at a much higher rate than the paraffin. The membrane can take a variety of forms suitable for a particular application. For example, the membrane can be in the form of a flat sheet, hollow tube or fiber, and the like. In this regard, various embodiments of the process contemplated herein can be used to replace C2 and C3 splitters, as hybrid membrane distillation units for olefin purification, for recovery of olefins from polypropylene vent streams or from fluid catalytic cracking (FCC) off-gas streams, or the like. The process can also be used for the production of polymer grade propylene, thus offering significant energy, capital, and operating cost savings compared to conventional distillation.

The olefin/paraffin separation process using the facilitated transport membrane comprising a carboxylic acid functional group containing polyimide wherein the carboxylic acid functional groups are ion-exchanged or chelated with metal cations such as silver (I) or copper (I) cations starts by contacting a first surface of the membrane with an olefin/paraffin feed. The olefin may comprise, for example, propylene or ethylene and the paraffin may comprise propane or ethane, respectively. The olefin/paraffin feed comprises a first concentration of olefin and a first concentration of paraffin depending on the application for which the membrane separation is used. For example, a propane dehydrogenation process typically provides a feed containing about 35 mass percent propylene, whereas a feed from an FCC unit generally contains about 75 mass percent propylene. The flow rate and temperature of the olefin/paraffin feed have those values that are suitable for a desired application. Next, a permeate is caused to flow through the membrane and from a second surface of the membrane. Because the facilitated transport membrane comprising a carboxylic acid functional group containing polyimide wherein the carboxylic acid functional groups are ion-exchanged or chelated with metal cations such as silver (I) or copper (I) cations for olefin/paraffin separations is much more selective to the olefin than to the paraffin, the permeate has a concentration of olefin that is higher than the concentration of the olefin in the feed. In one exemplary embodiment, the concentration of the olefin in the permeate is 99.5 mass percent. In addition, while some paraffin may permeate through the membrane, the permeate has a concentration of paraffin that is less than the concentration of the paraffin in the feed. The permeate can then be removed from the second surface of the membrane. As the permeate passes through the membrane, a retentate or residue, which has not permeated the membrane, is removed from the first surface of the membrane. The retentate has a concentration of olefin that is lower than the concentration of olefin in the feed and lower than the concentration of the permeate. The retentate also has a concentration of paraffin that is higher than a concentration of paraffin that is in the feed.

EXAMPLES

The following examples are provided to illustrate one or more preferred embodiments of the invention, but are not limited embodiments thereof. Numerous variations can be made to the following examples that lie within the scope of the invention.

Example 1

Preparation of Silver (I) Cation Exchanged/Chelated Poly(2,2'-bis-(3,4-dicarboxyphenyl)hexafluoropropane dianhydride-3,5-diaminobenzoic acid-3, 3',5,5'-tetramethyl-4,4'-methylene dianiline) Polyimide Facilitated Transport Membrane 1) Synthesis of carboxylic acid containing poly(2, 2'-bis-(3,4-dicarboxyphenyl)hexafluoropropane dianhydride-3,5-diaminobenzoic acid-3,3',5,5'-tetramethyl-4,4'-methylene dianiline) polyimide (Abbreviated as PI-150) polyimide The aromatic carboxylic acid containing poly(2,2'-bis-(3, 4-dicarboxyphenyl)hexafluoropropane dianhydride-3,5-diaminobenzoic acid-3,3 ', 5,5'-tetramethyl-4,4'-methylene dianiline) polyimide (abbreviated as PI-150) was synthesized from 2,2'-bis-(3,4-dicarboxyphenyl)hexafluoropropane dianhydride (6FDA) and a mixture of 3,5-diaminobenzoic acid (3,5-DBA) and 3,3',5,5'-tetramethyl-4,4'-methylene dianiline (TMMDA) (molar ratio of 3,5-DBA/TMMDA=2:1) in dimethylacetamide (DMAc) polar solvent by a two-step process involving the formation of the poly (amic acid) followed by a solution imidization process. Acetic anhydride was used as the dehydrating agent and pyridine was used as the imidization catalyst for the solution imidization reaction. For example, a 250 mL three-neck round-bottom flask equipped with a nitrogen inlet and a mechanical stirrer was charged with 9.0 g of 3,5-DBA, 7.6 g of TMMDA and 36.2 g of DMAc. Once 3,5-DBA and TMMDA monomers were fully dissolved, 41.2 g of 6FDA solid powder was added to the solution of 3,5-DBA and TMMDA stepwise under stirring in the flask. 155 g of DMAc was added to the solution after the 6FDA powder was added. The reaction mixture was mechanically stirred for 24 hours at ambient temperature to give a viscous poly(amic acid) solution. Then 20.8 g of acetic anhydride was added slowly to the reaction mixture under stirring followed by the addition of 30.8 g of pyridine to the reaction mixture. The reaction mixture was mechanically stirred for an additional 2.0 hours at 90° C. to yield a polyimide designated as PI-150 for the purpose of this application. The PI-150 product in a fine fiber form was recovered by slowly precipitating the reaction mixture into a large amount of methanol and water mixture. The resultant PI-150 polyimide fibers were then thoroughly rinsed with methanol and dried in a vacuum oven at 200° C. for 48 hours.

2) Fabrication of Asymmetric Integrally Skinned PI-150 Membrane

A PI-150 membrane casting dope containing PI-150 polyimide synthesized in step 1), NMP, 1,3-dioxolane, glycerol and n-decane was cast on a highly porous non-selective symmetric woven Nylon 6,6 fabric backing at a casting speed of 4 fpm at room temperature. The cast membrane was evaporated for 20 seconds to form the nascent asymmetric integrally-skinned flat sheet PI-150 membrane. The membrane was immersed into a cold water coagulation tank and then immersed into a hot water tank to remove the trace amount of organic solvents in the membrane. Finally the wet membrane was wound up on a core roll.

3) Preparation of 3 MAg+/PI-150 Facilitated Transport Membrane

The skin layer surface of the wet PI-150 membrane was immersed in a 3M $AgNO_3$ aqueous solution for 2.5 h and then the $AgNO_3$ aqueous solution was removed from the membrane surface to form the Ag+ exchanged/chelated PI-150 facilitated transport membrane (abbreviated as 3 MAg+/PI-150 for 3M $AgNO_3$ aqueous solution treated PI-150 membrane).

Example 2

Preparation of Silver (I) Cation Exchanged/Chelated Poly(2,2'-bis-(3,4-dicarboxyphenyl)hexafluoropropane dianhydride-3,5-diaminobenzoic acid-3, 3'-dihydroxy-4,4'-diamino-biphenyl) Polyimide Facilitated Transport Membranes 1) Synthesis of carboxylic acid containing poly(2, 2'-bis-(3,4-dicarboxyphenyl)hexafluoropropane dianhydride-3,5-diaminobenzoic acid-3,3'-dihydroxy-4,4'-diamino-biphenyl) polyimide (Abbreviated as PI-50) polyimide The aromatic carboxylic acid containing poly(2,2'-bis-(3, 4-dicarboxyphenyl)hexafluoropropane dianhydride-3,5-diaminobenzoic acid-3,3'-dihydroxy-4,4'-diamino-biphenyl) polyimide (abbreviated as PI-50) was synthesized from 6FDA and a mixture 3,5-DBA and 3,3'-dihydroxy-4,4'-diamino-biphenyl (HAB) (molar ratio of 3,5-DBA/HAB=1: 4) in dimethylacetamide (DMAc) polar solvent by a two-step process involving the formation of the poly(amic acid) followed by a solution imidization process. Acetic anhydride was used as the dehydrating agent and pyridine was used as the imidization catalyst for the solution imidization reaction. For example, a 1 L three-neck round-bottom flask equipped with a nitrogen inlet and a mechanical stirrer was charged with 9.1 g of 3,5-DBA, 51.9 g of HAB and 660 g of DMAc. Once 3,5-DBA and HAB monomers were fully dissolved, 133.9 g of 6FDA solid powder was added to the solution of 3,5-DBA and HAB stepwise under stirring in the flask. 445 g of DMAc was added to the solution after the 6FDA powder was added. The reaction mixture was mechanically stirred for 24 hours at ambient temperature to give a viscous poly(amic acid) solution. Then 72.0 g of acetic anhydride was added slowly to the reaction mixture under stirring followed by the addition of 104.4 g of pyridine to the reaction mixture. The reaction mixture was mechanically stirred for an additional 2.5 hours at 90° C. to yield a polyimide designated as PI-50 for the purpose of this application. The PI-50 product in a fine fiber form was recovered by slowly precipitating the reaction mixture into a large amount of methanol and water mixture. The resultant PI-50 polyimide fibers were then thoroughly rinsed with methanol and dried in a vacuum oven at 120° C. for 48 hours.

2) Fabrication of Asymmetric Integrally Skinned PI-50 Membrane

A PI-50 membrane casting dope containing PI-50 polyimide synthesized in step 1), NMP, 1,3-dioxolane, glycerol and n-decane was cast on a highly porous non-selective symmetric woven Nylon 6,6 fabric backing at a casting speed of 4 fpm at room temperature. The cast membrane was evaporated for 20 seconds to form the nascent asymmetric integrally-skinned flat sheet PI-50 membrane. The membrane was immersed into a cold water coagulation tank and then immersed into a hot water tank to remove the trace amount of organic solvents in the membrane. Finally the wet membrane was wound up on a core roll.

3) Preparation of Ag+/PI-50 Facilitated Transport Membranes

The skin layer surface of the wet PI-50 membrane was immersed in a 1M, 1.5M or 3M $AgNO_3$ aqueous solution for 2.5 h and then the $AgNO_3$ aqueous solution was removed from the membrane surface to form the Ag+ exchanged/chelated PI-50 facilitated transport membranes (abbreviated as 1 MAg+/PI-50 for 1.0M $AgNO_3$ aqueous solution treated PI-50 membrane, 1.5 MAg+/PI-50 for 1.5M $AgNO_3$ aqueous solution treated PI-50 membrane, and 3 MAg+/PI-50 for 3M $AgNO_3$ aqueous solution treated PI-50 membrane).

Comparative Example 1

Preparation of Silver (I) Cation Impregnated Polyethersulfone Facilitated Transport Membrane

1) Fabrication of Asymmetric Integrally Skinned Polyethersulfone (PES) Membrane A PES membrane casting dope containing PES, NMP, 1,3-dioxolane, glycerol and n-decane was cast on a highly porous non-selective symmetric woven Nylon 6,6 fabric backing at a casting speed of 6 fpm at room temperature. The cast membrane was evaporated for 13 seconds to form the nascent asymmetric integrally-skinned flat sheet PES membrane. The membrane was immersed into a cold water coagulation tank and then immersed into a hot water tank to remove the trace amount of organic solvents in the membrane. Finally the wet membrane was wound up on a core roll.

2) Preparation of 3 MAg+/PES Facilitated Transport Membrane

The skin layer surface of the wet asymmetric integrally skinned PES membrane was immersed in a 3M $AgNO_3$ aqueous solution for 2.5 h and then the $AgNO_3$ aqueous solution was removed from the membrane surface to form the Ag+ impregnated PES facilitated transport membrane (abbreviated as 3 MAg+/PES for 3M $AgNO_3$ aqueous solution treated PES membrane).

Example 3

Evaluation of Propylene/Propane Separation Performance of the Facilitated Transport Membranes The 3 MAg+/PI-150, 3 MAg+/PI-50, and 3 MAg+/PES facilitated transport membranes were evaluated for propylene/propane separation at 35° C. under 791 kPa (100 psig) propylene/propane (30%/70%) mixed vapor phase feed pressure wherein the feed stream was bubbled through water at 35° C. The retentate flow rate was set at 708 scc/min. The results in Table 1 show that the new 3 MAg+/PI-150 and 3 MAg+/PI-50 facilitated transport membranes disclosed in the present invention have both high propylene (C3=) permeance of >145-199 GPU and high propylene/propane (C3=/C3) selectivity of 239-307. The propylene/propane permeation experiments also demonstrated that the new 3 MAg+/PI-150 and 3 MAg+/PI-50 facilitated transport membranes comprising carboxylic acid functional groups ion-exchanged or chelated with silver (I) cations disclosed in the present invention showed much more stable membrane performance than the comparative 3 MAg+/PES facilitated transport membrane without any carboxylic acid functional groups. The comparative 3 MAg+/PES facilitated transport membrane showed Knudsen flow without any propylene/propane selectivity under 791 kPa (100 psig) propylene/propane (30%/70%) mixed vapor phase feed pressure.

TABLE 1

Propylene/propane permeation test results of 3MAg+/PI-150, 3MAg+/PI-50, and 3MAg+/PES facilitated transport membranes [a]

| Membrane | $P_{C3=}/L$ (GPU) | $\alpha_{C3=/C3}$ |
|---|---|---|
| 3MAg+/PI-150 | 146.5 | 239 |
| 3MAg+/PI-50 | 198.9 | 307 |
| 3MAg+/PES | overflow | ~1 |

[a] Tested at 35° C., 790 kPa (100 psig) propylene/propane (30%/70%) mixed vapor feed pressure; feed stream was bubbled through water at 35° C.; retentate flow rate was set at 708 scc/min; data collected after 1 h of testing; 1 GPU = $10^{-6}$ $cm^3$ (STP)/$cm^2$ s (cm Hg).

Example 4

Evaluation of 1 MAg+/PI-50, 1.5 MAg+/PI-50, 3 MAg+/PI-50 Facilitated Transport Membranes with Different Silver (I) Cation Contents for Propylene/Propane Separation The 1 MAg+/PI-50, 1.5 MAg+/PI-50, 3 MAg+/PI-50 facilitated transport membranes with different silver (I) cation content disclosed in the present invention were evaluated for propylene/propane separation at 35° C. under 791 kPa (100 psig) propylene/propane (30%/70%) mixed vapor phase feed pressure wherein the feed stream was bubbled through water at 35° C. The retentate flow rate was set at 708 scc/min. The results in Table 2 show that the 1.5 MAg+/PI-50 facilitated transport membrane prepared from 1.5M $AgNO_3$ aqueous solution exhibits the highest propylene/propane selectivity and propylene permeance among the three membranes. The results in Table 2 show that the 1.5 MAg+/PI-50 facilitated transport membrane prepared from 1.5M $AgNO_3$ aqueous solution also exhibits high propylene/propane selectivity and propylene permeance with a high propylene concentration feed of 70% propylene and 30% propane.

TABLE 2

Propylene/propane permeation test results of 1MAg+/PI-50, 1.5MAg+/PI-50, and 3MAg+/PI-50 facilitated transport membranes

| Membrane | $P_{C3=}/L$ (GPU) | $\alpha_{C3=/C3}$ |
|---|---|---|
| 1MAg+/PI-50 [a] | 278.3 | 285 |
| 1.5MAg+/PI-50 [a] | 258.6 | 466 |

TABLE 2-continued

Propylene/propane permeation test results of 1MAg+/PI-50, 1.5MAg+/PI-50, and 3MAg+/PI-50 facilitated transport membranes

| Membrane | $P_{C3=}/L$ (GPU) | $\alpha_{C3=/C3}$ |
|---|---|---|
| 1.5MAg+/PI-50 [b] | 191.5 | ~1000 |
| 3MAg+/PI-50 [a] | 198.9 | 307 |

[a] Tested at 35° C., 790 kPa (100 psig) propylene/propane (30%/70%) mixed vapor feed pressure; feed stream was bubbled through water at 35° C.; retentate flow rate was set at 708 scc/min; data collected after 1 h of testing;
[b] Tested at 35° C., 790 kPa (100 psig) propylene/propane (70%/30%) mixed vapor feed pressure; feed stream was bubbled through water at 35° C.; retentate flow rate was set at 708 scc/min; data collected after 1 h of testing; 1 GPU = $10^{-6}$ cm$^3$ (STP)/cm$^2$ s (cm Hg).

SPECIFIC EMBODIMENTS

While the following is described in conjunction with specific embodiments, it will be understood that this description is intended to illustrate and not limit the scope of the preceding description and the appended claims.

A first embodiment of the invention is a facilitated transport membrane comprising a carboxylic acid functional group containing polyimide wherein the carboxylic acid functional groups are ion-exchanged or chelated with silver (I) or copper (I) cations wherein the silver (I) or copper (I) cation ion-exchanged or chelated carboxylic acid functional group containing polyimide comprises a plurality of repeating units of formula (I)

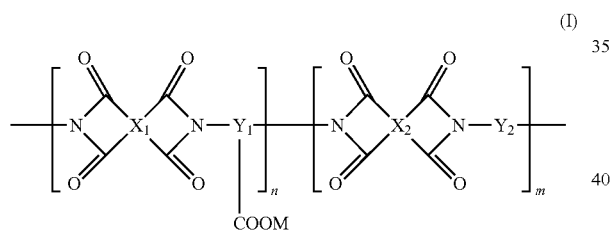

(I)

wherein $X_1$ and $X_2$ are selected from the group consisting of

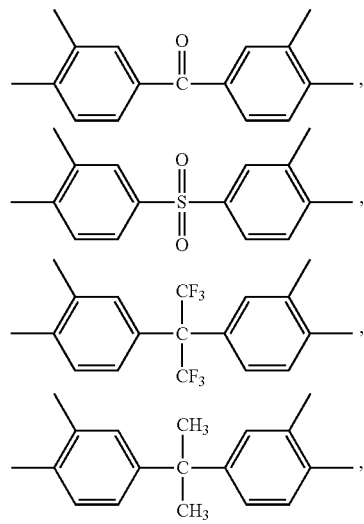

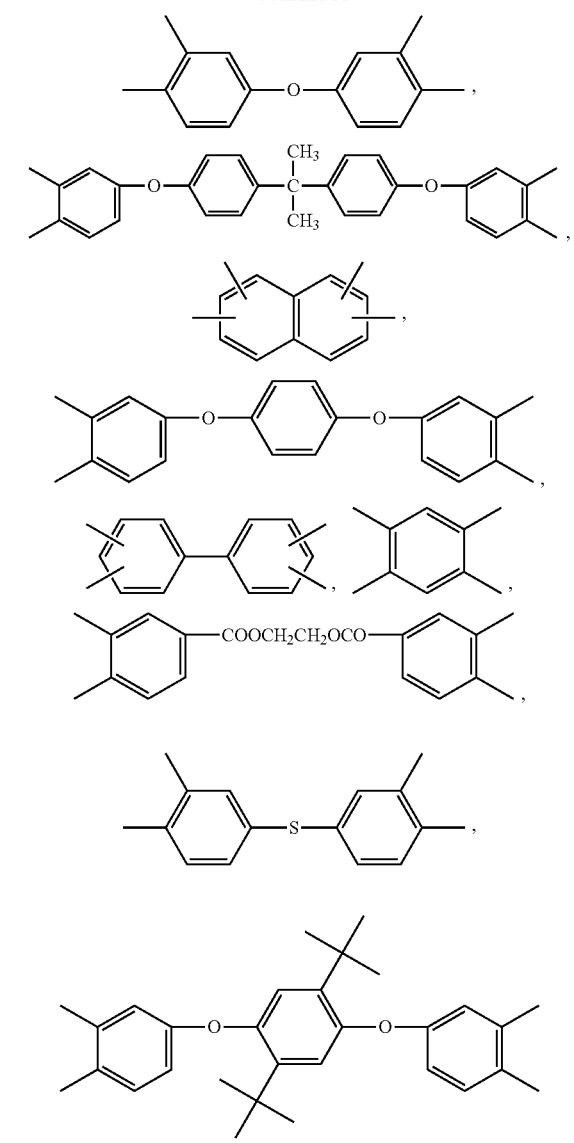

and mixtures thereof, wherein X1 and X2 may be the same or different from each other; wherein $Y_1$—COOM is selected from the group consisting of

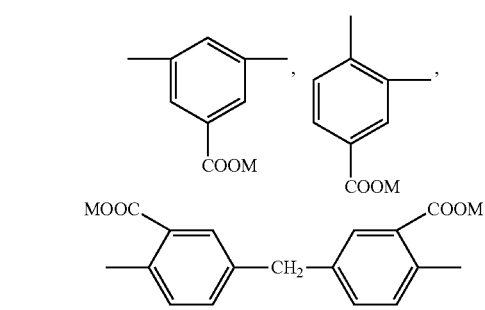

and mixtures thereof and wherein M is selected from a silver cation or a copper (I) cation; wherein Y2 is selected from the group consisting of

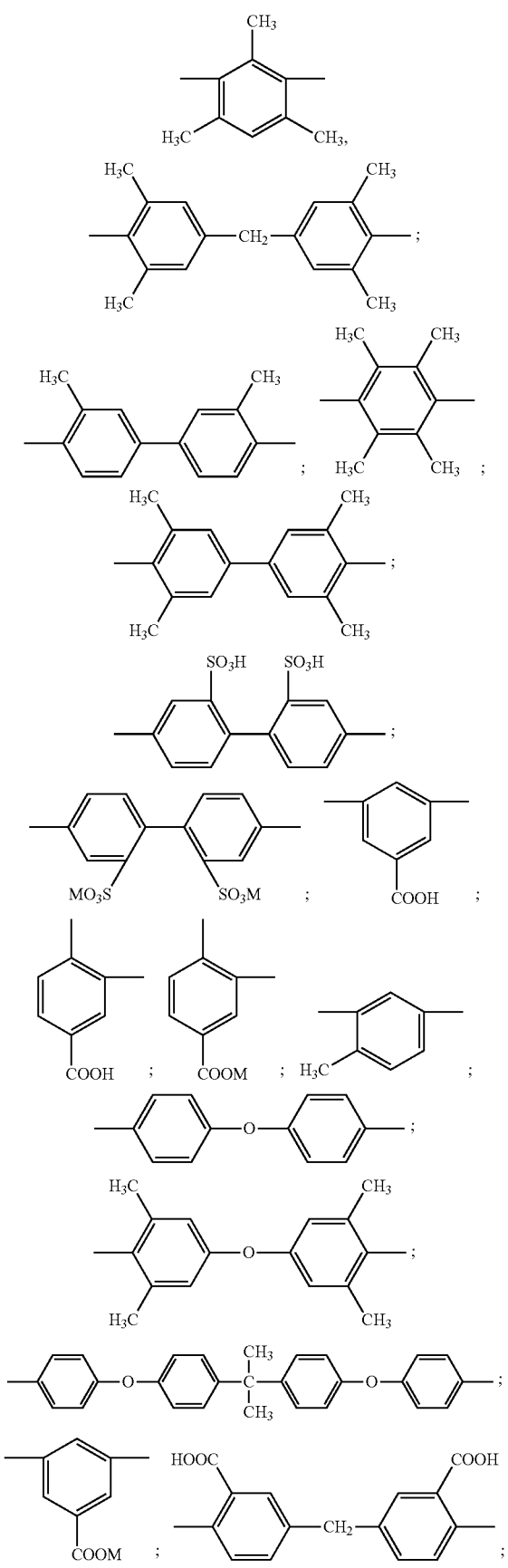

and mixtures thereof, —R'— is selected from the group consisting of and mixtures thereof, —R"— is selected from the group consisting of —H, COCH₃, and mixtures thereof, M is selected from a silver (I) cation or a copper (I) cation; wherein n and m are independent integers from 2 to 500; and wherein n/m is in a range of 1:0 to 1:10. An embodiment of the invention is one, any or all of prior embodiments in this paragraph up through the first embodiment in this paragraph wherein $X_1$ and $X_2$ are selected from the group consisting of and mixtures thereof. An embodiment of the invention is one, any or all of prior embodiments in this paragraph up through the first embodiment in this paragraph wherein $Y_1$—COOM is selected from the group consisting of

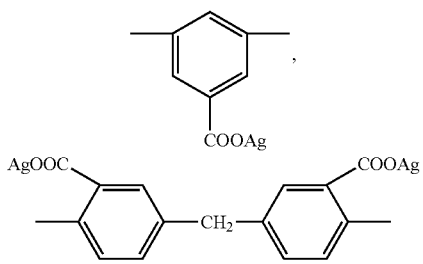

and mixtures thereof. An embodiment of the invention is one, any or all of prior embodiments in this paragraph up through the first embodiment in this paragraph wherein Y2 is selected from the group consisting of

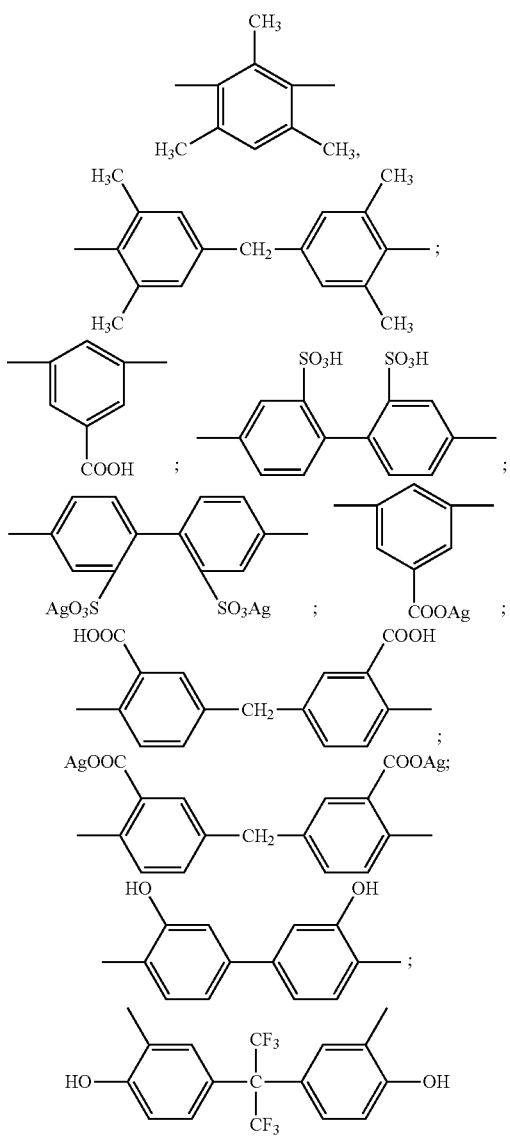

and mixtures thereof. An embodiment of the invention is one, any or all of prior embodiments in this paragraph up through the first embodiment in this paragraph wherein —R"— is selected from the group consisting of —H, COCH$_3$, and mixtures thereof.

A second embodiment of the invention is a method of making a high performance facilitated transport membrane comprising a carboxylic acid functional group containing polyimide wherein the carboxylic acid functional groups are ion-exchanged or chelated with metal cations such as silver (I) or copper (I) cations, the method comprising a) preparing an asymmetric carboxylic acid functional group containing polyimide flat sheet or hollow fiber membrane with either an asymmetric integrally skinned or a thin film composite membrane structure, wherein at least the top selective layer of the membrane comprises a carboxylic acid functional group containing polyimide; and b) preparation the facilitated transport membrane by ion-exchanging or chelating the carboxylic acid functional groups on the polyimide polymer of the asymmetric carboxylic acid functional group containing polyimide flat sheet or hollow fiber membrane prepared in step a) with silver (I) or copper (I) cations. An embodiment of the invention is one, any or all of prior embodiments in this paragraph up through the second embodiment in this paragraph wherein the top selective layer surface of the asymmetric carboxylic acid functional group containing polyimide flat sheet or hollow fiber membrane is soaked in a metal cation aqueous solution comprising silver nitrate (AgNO$_3$) aqueous solution for a sufficient time to form the facilitated transport membrane comprising metal cation ion-exchanged or chelated carboxylic acid functional group containing polyimide.

A third embodiment of the invention is an olefin/paraffin separation process comprising (a) contacting a first surface of a membrane with an olefin/paraffin feed, wherein the membrane comprises a carboxylic acid functional group containing polyimide wherein the carboxylic acid functional groups are ion-exchanged or chelated with silver (I) or copper (I) cations, (b) causing a permeate to flow through the membrane and from a second surface of the membrane wherein the permeate has a higher concentration of olefin than the olefin/paraffin feed, and then (c) removing a retentate from the first surface of the membrane wherein the retentate has a lower concentration of olefin than the permeate and wherein the retentate has a higher concentration of paraffin than the permeate. An embodiment of the invention is one, any or all of prior embodiments in this paragraph up through the third embodiment in this paragraph wherein the permeate comprises 99.5 mass percent olefin. An embodiment of the invention is one, any or all of prior embodiments in this paragraph up through the third embodiment in this paragraph wherein the facilitated transport membrane comprises a carboxylic acid functional group containing polyimide wherein the carboxylic acid functional groups are ion-exchanged or chelated with silver (I) or copper (I) cations wherein the silver (I) or copper (I) cation ion-exchanged or chelated carboxylic acid functional group containing polyimide comprises a plurality of repeating units of formula (I)

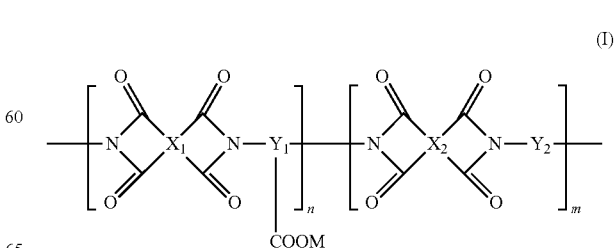

wherein $X_1$ and $X_2$ are selected from the group consisting of
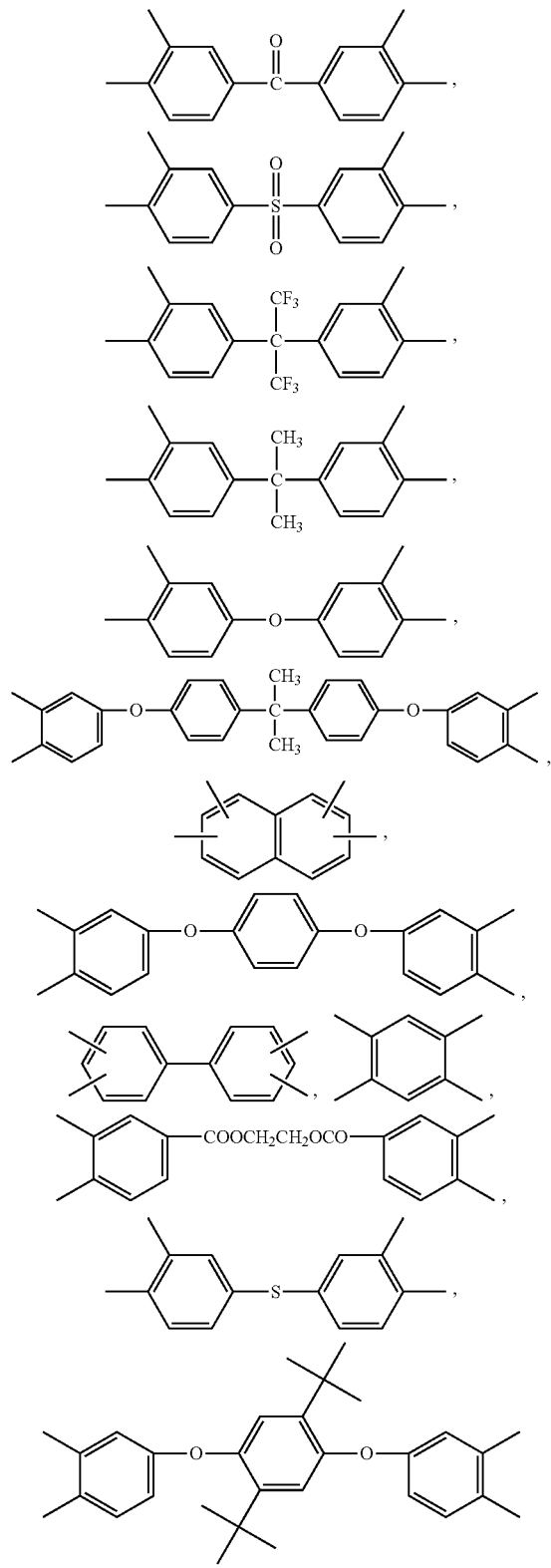
and mixtures thereof, wherein X1 and X2 may be the same or different from each other; wherein $Y_1$—COOM is selected from the group consisting of
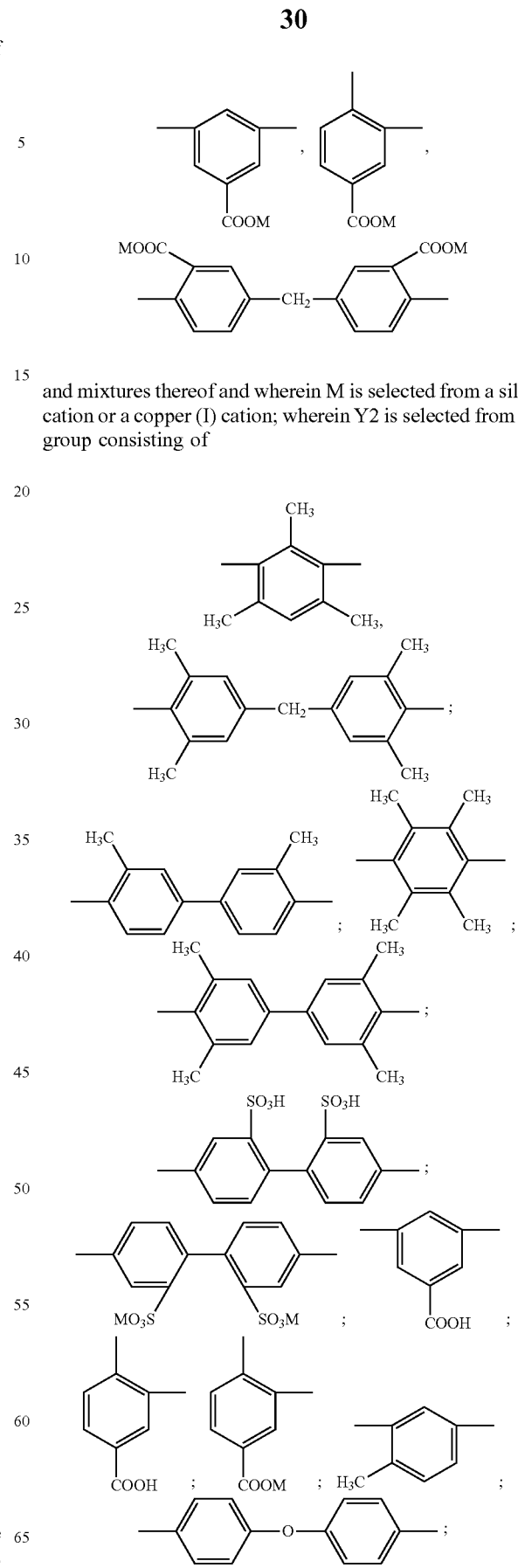
and mixtures thereof and wherein M is selected from a silver cation or a copper (I) cation; wherein Y2 is selected from the group consisting of

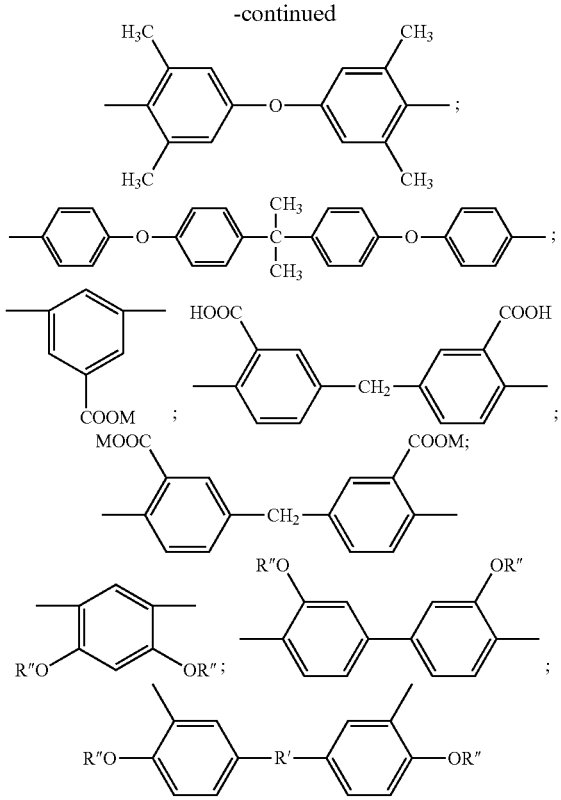

and mixtures thereof, —R'— is selected from the group consisting of

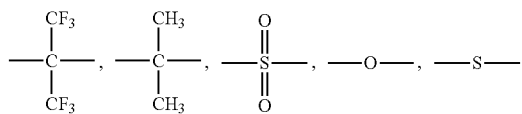

and mixtures thereof, —R"— is selected from the group consisting of —H, COCH₃, and mixtures thereof, M is selected from a silver cation or a copper (I) cation; wherein n and m are independent integers from 2 to 500; and wherein n/m is in a range of 1:0 to 1:10.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. An olefin/paraffin separation process comprising:
   (a) contacting a first surface of a membrane with an olefin/paraffin feed, wherein said membrane comprises a carboxylic acid functional group containing polyimide wherein the carboxylic acid functional groups are ion-exchanged or chelated with silver (I) or copper (I) cations;
   (b) causing a permeate to flow through said membrane and from a second surface of said membrane wherein the permeate has a higher concentration of olefin than said olefin/paraffin feed; and
   (c) removing a retentate from said first surface of said membrane wherein the retentate has a lower concentration of olefin than the permeate and wherein the retentate has a higher concentration of paraffin than the permeate.

2. The olefin/paraffin separation process of claim 1 wherein said permeate comprises 99.5 mass percent olefin.

3. The olefin/paraffin separation process of claim 1 wherein the facilitated transport membrane comprises a carboxylic acid functional group containing polyimide wherein the carboxylic acid functional groups are ion-exchanged or chelated with silver (I) or copper (I) cations wherein the silver (I) or copper (I) cation ion-exchanged or chelated carboxylic acid functional group containing polyimide comprises a plurality of repeating units of formula (I)

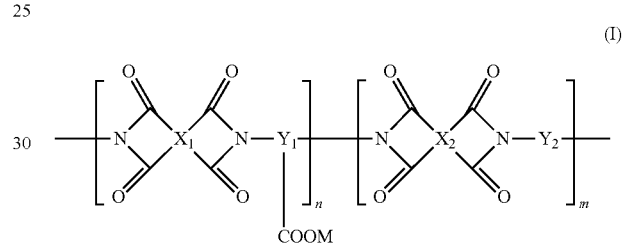

wherein X₁ and X₂ are selected from the group consisting of

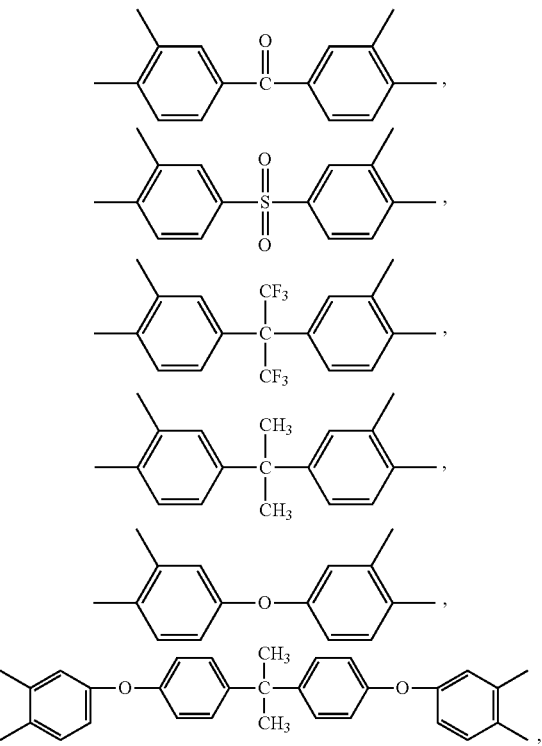

-continued

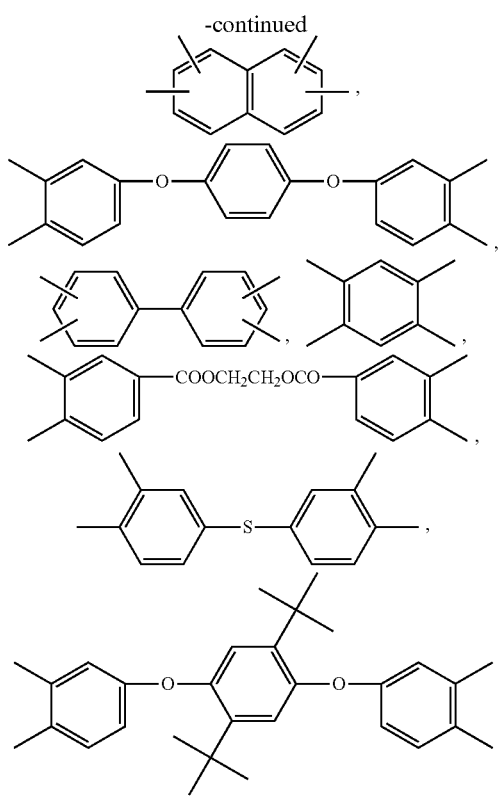

and mixtures thereof, wherein X1 and X2 may be the same or different from each other; wherein $Y_1$—COOM is selected from the group consisting of

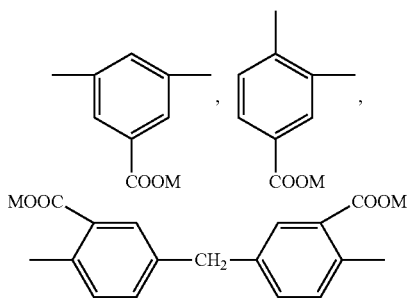

and mixtures thereof and wherein M is selected from a silver (I) cation or a copper (I) cation; wherein Y2 is selected from the group consisting of

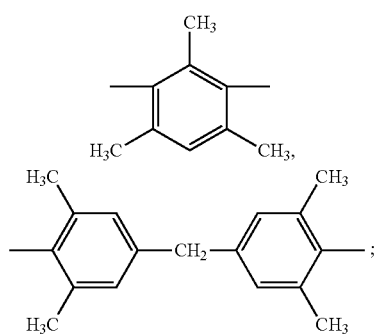

-continued

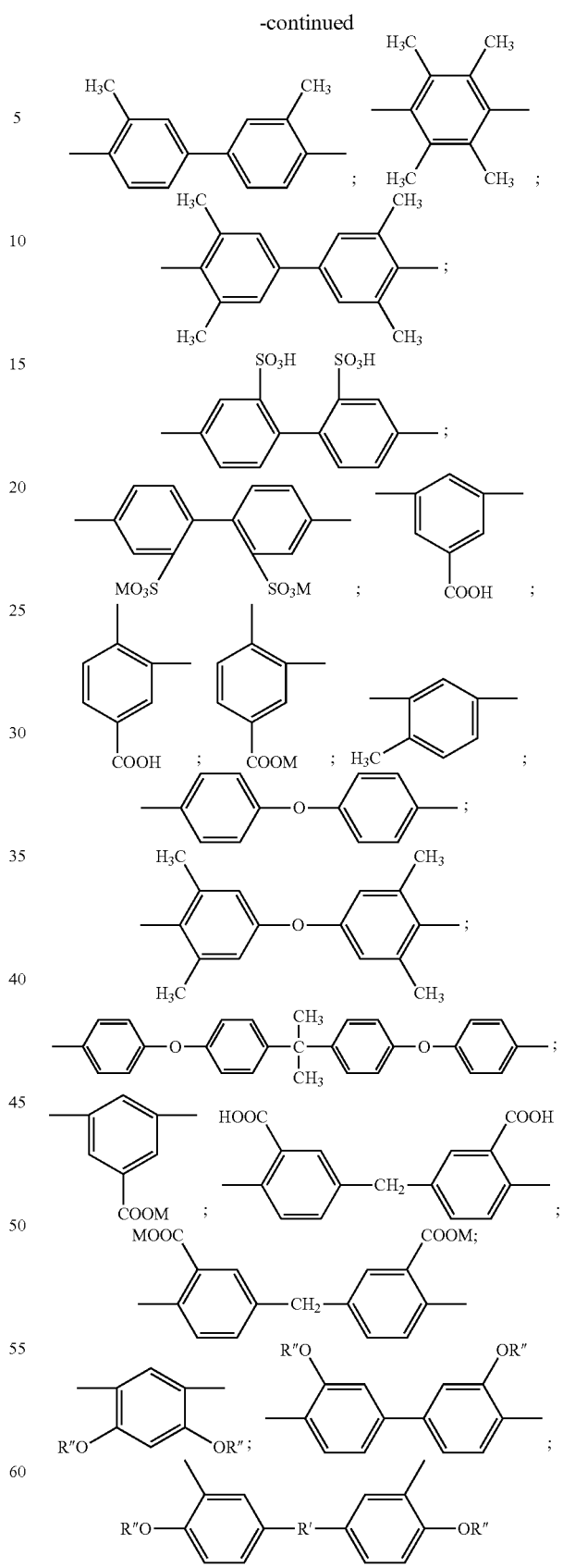

and mixtures thereof, —R'— is selected from the group consisting of

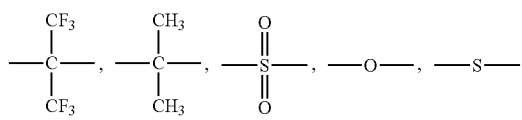

and mixtures thereof, —R"— is selected from the group consisting of —H, COCH$_3$, and mixtures thereof, M is selected from a silver (I) cation or a copper (I) cation; wherein n and m are independent integers from 2 to 500; and wherein n/m is in a range of 1:0 to 1:10.

4. The olefin/paraffin separation process of claim 3 wherein X$_1$ and X$_2$ are selected from the group consisting of

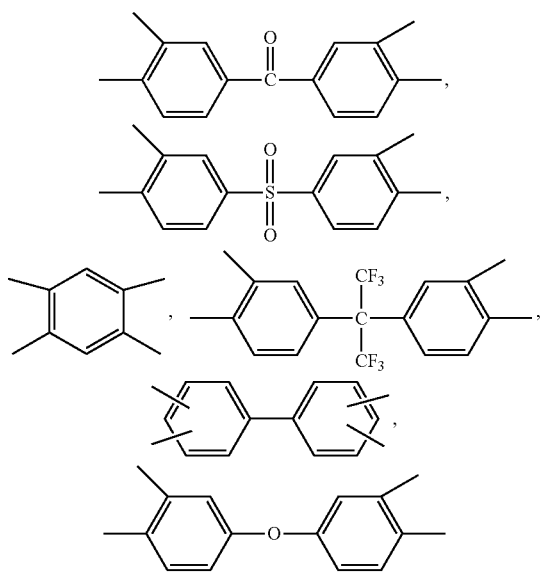

and mixtures thereof.

5. The olefin/paraffin separation process of claim 3, wherein Y$_1$—COOM is selected from the group consisting of

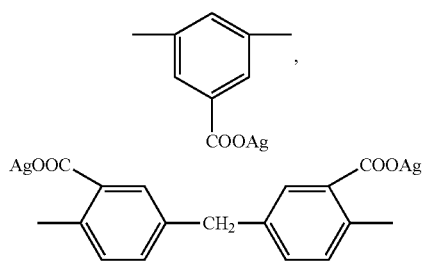

and mixtures thereof.

6. The olefin/paraffin separation process of claim 3 wherein Y2 is selected from the group consisting of

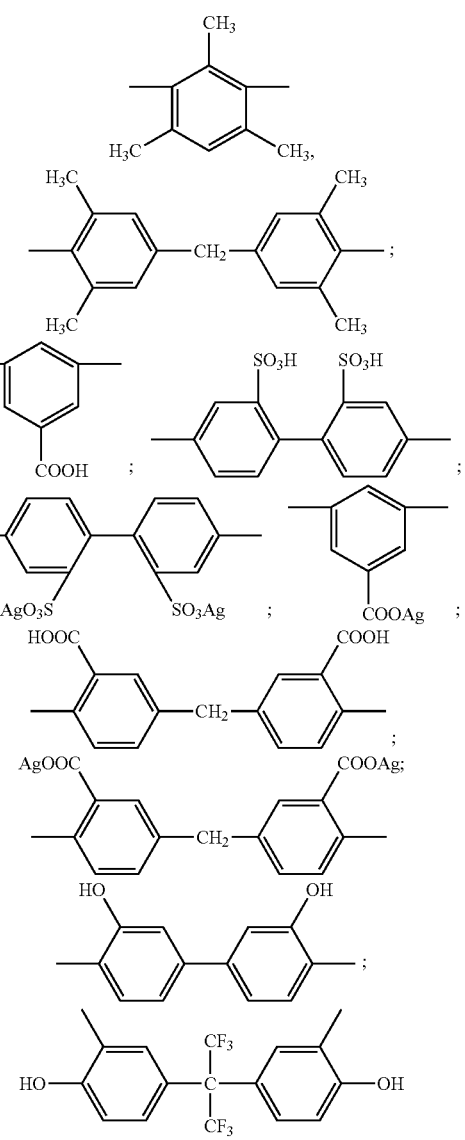

and mixtures thereof.

7. The olefin/paraffin separation process of claim 3 wherein —R"— is selected from the group consisting of —H, COCH$_3$, and mixtures thereof.

8. The olefin/paraffin separation process of claim 1 wherein said membrane is in a form of a flat sheet, hollow tube or hollow fiber.

9. The olefin/paraffin separation process of claim 1 wherein the olefin/paraffin feed is a gaseous stream produced from steam cracking, catalytic cracking or dehydration of paraffins.

* * * * *